United States Patent
Chang et al.

(10) Patent No.: US 7,851,215 B2
(45) Date of Patent: Dec. 14, 2010

(54) RECOMBINANT PROTEIN COMPRISING STARCH BINDING DOMAIN AND USE THEREOF

(75) Inventors: Margaret Dah-Tsyr Chang, Hsinchu (TW); Chia-Chin Sheu, Taoyuan County (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 0 days.

(21) Appl. No.: 12/643,304

(22) Filed: Dec. 21, 2009

(65) Prior Publication Data

US 2010/0099855 A1 Apr. 22, 2010

Related U.S. Application Data

(62) Division of application No. 11/070,271, filed on Mar. 3, 2005, now Pat. No. 7,662,918.

(51) Int. Cl.
*C12N 15/00* (2006.01)
*C07H 21/02* (2006.01)

(52) U.S. Cl. .................................. 435/320.1; 536/23.1
(58) Field of Classification Search ................ 536/23.1; 435/320.1

See application file for complete search history.

*Primary Examiner*—Maryam Monshipouri
(74) *Attorney, Agent, or Firm*—WPAT, P.C.; Anthony King

(57) ABSTRACT

A recombinant protein is prepared comprising a polypeptide of interest and a starch binding domain (SBD). The said SBD is obtainable from glucoamylase of fungi genus *Rhizopus*. The said recombinant protein comprising the said SBD can be purified by contacting with an affinity matrix such as starch, the SBD binds to the affinity matrix to isolate the recombinant protein. The recombinant protein can be purified by separating the association between the SBD and the affinity matrix by acid, alkaline, salt, or sugar. The polypeptide of interest may be an antibody, an antigen, a therapeutic compound, an enzyme, or a protein and may apply in pathogen destruction, vaccine producing, and oral care product manufacturing. The SBD further provides as a tool to screen or identify polysaccharides.

10 Claims, 6 Drawing Sheets

RECOMBINANT PROTEIN COMPRISING STARCH BINDING DOMAIN AND USE THEREOF

CROSS-REFERENCE TO RELATED APPLICATIONS

This application is a Divisional of U.S. patent application Ser. No. 11/070,271 filed on Mar. 3, 2005, issued on Feb. 16, 2010 as now U.S. Pat. No. 7,662,918, which is hereby incorporated by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

This invention relates to functions of starch binding domain (SBD) of glucoamylase in fungi *Rhizopus* spp. A recombinant protein comprising the SBD can be produced and purified by using the SBD as a tag. This invention further relates to a novel method and a kit to purify the recombinant protein and novel applications of the SBD and the recombinant protein.

BACKGROUND OF THE INVENTION

Production of proteins by expression in microbial systems has become a significant source of high value, medically important proteins. Purification and recovery of recombinant proteins are major considerations in the design of a fermentation process. While traditional methods of protein purification can be used to isolate a product, improved methods include the use of recombinant proteins. Recombinant proteins can be purified by affinity chromatography, the desired component of the recombinant protein being purified by virtue of its covalent attachment to a polypeptide, which binds to an affinity matrix.

Certain systems exist for isolating proteins by the principle of affinity chromatography.

U.S. Pat. No. 5,643,758 describes a system comprising maltose-binding protein (MBP). A cloned gene is inserted into a pMAL vector down-stream from the malE gene, which encodes MBP. The vector is transformed to a host cell, then the recombinant protein can express in the host cell. The cell lysate or media fraction is loaded to a column containing affinity matrix amylose and washed several times, then using a large amount of maltose to elute the recombinant protein.

U.S. Pat. No. 5,202,247 describes a system comprising cellulose-binding domain. A cellulose column can be used to purify the recombinant protein which contains cellulose-binding domain. The cell lysate or media fraction is loaded to the column and washed. The interaction between cellulose-binding domain and cellulose appears to be driven by hydrophobic interaction at neutral pH. The general method for elution used low polarity solvents such as ethylene glycol, prior to removal of the low polarity solvents by dialysis and filtration.

A chitin-binding domain and an inducible-splicing linker region can be fused in the C-terminus or N-terminus of a target protein. The cell lysate or media fraction is loaded to the column and washed. The chitin-binding domain binds to the chitin column to immobilize the recombinant protein. In the presence of thiols such as DTT or cysteine, the linker region undergoes specific self-cleavage which releases the target protein from the chitin-bound chitin-binding domain.

These current protein purification systems have some disadvantages. The purification processes are inconvenient and laborious. The columns used in purification are expensive. Limitations for protein purification of these systems include unable to isolate the recombinant protein in certain conditions such as EDTA-containing samples as well as the current protein tags being used are relatively large as compared to the target protein bigger than that of this invention.

SUMMARY OF THE INVENTION

This invention provides a starch binding domain comprising a characteristic dissociation constant ($K_d$) of 0.5~2.29 µM. This invention also provides a recombinant protein comprising a polypeptide and a starch-binding domain of the invention. This invention also provides an expression vector comprises a gene encoding starch binding domain of the invention. This invention also provides a host cell transformed or transfected with a vector for the replication and expression of DNA encoding the recombinant protein comprising a polypeptide of interest and a starch-binding domain of the invention. This invention further provides a method for purifying a recombinant protein comprising a polypeptide and a starch binding domain of the invention from a biological liquid, which method comprises: (a) applying the biological liquid containing the recombinant protein directly to an affinity matrix; (b) eluting the affinity matrix by eluent; and (c) dialyzing the eluent. This invention further provides a kit for purifying a recombinant protein comprises an expression vector used to express the recombinant protein. This invention further provides a method of sorting carbohydrate-containing molecule in a sample containing various carbohydrate-containing molecules comprises: (a) preparing a set of separator with different $K_d$ values of carbohydrate binding domain; (b) putting the sample into the set of separator; and (c) sorting the molecule into bound and unbound groups in accordance with different $K_d$ values.

DETAILED DESCRIPTION OF THE INVENTION

Figure 1:
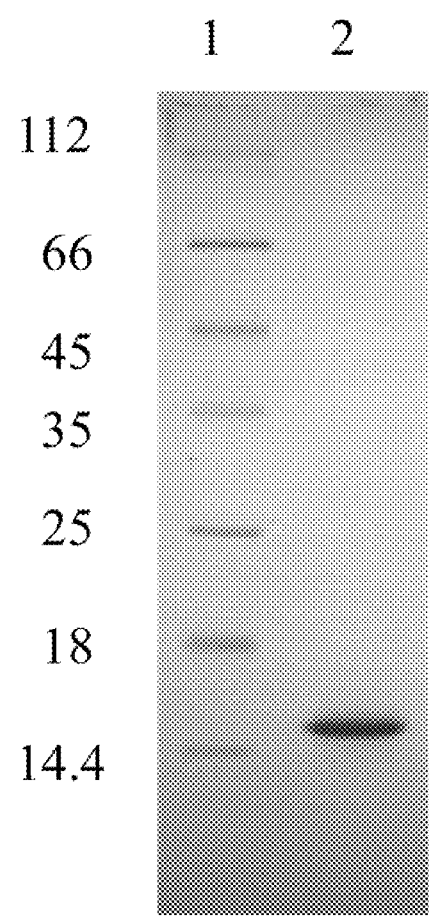
FIG. 1 illustrates purification of SBD-6H using starch. The purified SBD-6H is subjected to SDS/PAGE (15% gel) and the gel is stained with Coomassie Brilliant Blue R-250 for protein detection. Lane 1, molecular mass standards (molecular masses indicated at the left); lane 2, Two microgram of SBD-6H that is purified on corn starch.

The present invention is provided with a specially high affinity and strong binding ability of a starch binding domain (SBD) of an enzyme glucoamylase from fungal genus *Rhizopus*, especially in *Rhizopus oryzae*. The glucoamylase (1,4-α-D-glucan glucohydrolase, EC 3.2.1.3) is a multidomain exo-acting glycoside hydrolase that catalyzes the release of β-D-glucose from the non-reducing ends of starch and related substrates. Glucoamylase is a modular protein comprising a catalytic domain (CD), and a starch binding domain (SBD), categorized to carbohydrate-binding modules (CBMs). The two independent domains are connected with an O-glycosylated linker (for detailed information, see URL afmb.cnrs-mrs.fr/CAZY/index.html; Boraston et al. Biochem J (2004) 382: 769-781; Fang et al. Protein Engineering (1998) 11:119-126; Sauer et al. Biochemistry (2001) 40: 9336-9346).

The CBMs mediate the interaction of glycoside hydrolases with substrates by concentrating the catalytic domains on the surface of insoluble polysaccharides (Bolam et al. Biochem J (1998) 331:775-781). The significant decreases in the activity of enzymes on insoluble but not soluble polysaccharides are observed by both proteolytic excision and truncation of CBMs from glycoside hydrolases (Charonck et al. Biochemistry (2000) 39:5013-5021; Ali et al. Biosci Biotechnol Biochem (2001) 65:41-47). Different from all C-terminal SBDs belonging to the CBMs family 20, the N-terminal SBDs of glucoamylases are classified as members of CBM family 21. At present, glucoamylases from *Rhizopus oryzae*, *Arxula adeninivorans* and *Mucor circinelloides* have the CBM family 21 starch binding domain located at the N-termini (Houghton-Larsen et al. Appl Microbiol Biotechnol (2003) 62: 210-217).

Comparison of the amino acid sequences of SBDs from these species and *A. niger* SBD shows that the homology between *R. oryzae* SBD and that of *A. adeninivorans, M. circinelloides*, and *Aspergillus. niger* is 35.4%, 67.3% and 26.1%, respectively. The difference of the protein sequences between CBM 20 and CBM 21 families implies that these SBDs are distinct in biological and biochemical functions.

The polypeptide of the SBD according to the invention can be obtainable from *Rhizopus* spp. The embodiment in this invention is *Rhizopus oryzae*. The amino acid sequences of SBDs obtainable from Simpson strain, wild type strain and a strain in U.S. Pat. No. 4,863,864 as shown in SEQ ID NOS: 1, 2, and 3 are different from each other. The SBDs of *Rhizopus oryzae* including allelic variation and derivatives have high affinity with starch and express strong starch-binding ability as compared with known SBDs.

In this invention, the DNA molecule encoding SBD is amplified by PCR. The PCR product is cloned into an expression vector and transformed into a host cell. Transformed host cells are induced to express SBD. Cell lysate is harvested and the supernatant is applied directly to the affinity matrix, then washed and eluted. The elution buffer can be salt, sugar, and/or acidic or alkaline. The SBD of *Rhizopus* spp. is first characterized in this invention to be stable in a wide range of pH and dissociate with starch in acidic or alkaline environments. In this invention, it is first identified that the dissociation constant ($K_d$) value of SBD in *Rhizopus* spp is lower than that of known species such as *Aspergillus niger*, and the starch binding ability of SBD in *Rhizopus* spp is much higher than that of known species such as *Aspergillus niger*. The preferred embodiment of the dissociation constant ($K_d$) value of SBDs in *Rhizopus* to granular corn starch is 0.5~2.29. The more preferred embodiment of the dissociation constant ($K_d$) value is 1.0~2.0. The further preferred embodiment of the dissociation constant ($K_d$) value is 1.3~1.6. The most preferred embodiment of the dissociation constant ($K_d$) value is 1.43.

This invention also provides a recombinant protein comprising a SBD of this invention and a polypeptide of interest. A gene encoding a polypeptide of interest is cloned into the SBD-expression vector as previously described. The cloning site is neighboring the sbd gene, either upstream or downstream of sbd gene. The SBD can be linked with the polypeptide in N-terminus or in C-terminus. This fusion gene expression vector can be transformed into a host cell, including bacteria, yeast, fungi, mammalian cell, or insect cell. The recombinant protein can be expressed in the transformed cell. Thus, this recombinant protein according to this invention can be purified by using starch as affinity matrix, via the association between SBD and starch.

The affinity matrix used in recombinant protein purification can be a component recognized by SBD. The SBD according to this invention can bind the glucose-glucose linkage structure, both α-1,4- and α-1,6-linkage. By this characteristic, the affinity matrix can be a component containing the formula:

$$(X\text{-}X)_n$$

X means glucose molecule, the linkage between glucose and glucose is α-1,4-linkage or α-1,6-linkage and n is 1 or more than 1. One component contains the former structure in any part structure such as main chain, side chain, or modified residue can be selected to be affinity matrix. For example, starch, mannose, dextran, or glycogen can be affinity matrix.

This invention provides a recombinant protein purification method by using a starch binding domain of the invention and an affinity matrix. The method comprises (a) applying the biological liquid containing the recombinant protein directly to an affinity matrix; (b) eluting the affinity matrix by elution buffer; and (c) dialyzing the eluent. This invention can be used to increase the production, activity, stability or solubility of recombinant proteins and polypeptides. This invention is suitable for large-scale protein purification with wide range of optimal pH. The yield of the purified recombinant protein is high with sufficient purity (greater than 95%). The advantages of this invention also includes that various elution buffers and affinity matrices can be chosen and be available commercially, the former includes sugar, salt, and/or pH and the latter includes starch, mannose, dextran, or glycogen. Further, SBD is a smaller tag than commonly used fusion protein tags including glutathione S-tansferase (GST), MBP, thioredoxin (Trx), or Nus, and this system is appropriated to purify particular samples comprising EDTA-, EGTA-, or DTT-containing sample.

This invention provides a kit to purify a recombinant protein and applications thereof. The kit comprises an expressing vector to express the recombinant protein according this invention. The kit further comprises an affinity matrix and an elution buffer. The affinity matrix can bind SBD to isolate the recombinant protein. The elution buffer is used to separate the association between SBD and affinity matrix.

The polypeptide of interest as previously described may be an antibody, an antigen, a therapeutic compound, an enzyme, or a protein. Via the kit provided by this invention, these products can be over-produced and purified rapidly. The applications of these products are described as follows.

The polypeptide of interest may be an antibody or a therapeutic compound, which targets and allows damage/destruction or detection of the pathogen. This invention allows the antibody or the therapeutic compound easily purified by using starch and can be further isolated by cleaving the SBD region. The purified product can be used for therapy or detection of pathogens.

The polypeptide of interest may be an antigen or an antigenic compound, which can induce immune responses. This fusion protein can bind to an affinity matrix such as starch. The fusion protein-bound starch can be supplied as source of foods. When eating the fusion protein-bound starch, users will gain vaccination effect. The fusion protein-bounded starch can be an oral vaccine.

This invention further provides an application relates an oral care composition. The oral care composition comprises the SBD of the invention, wherein said composition is selected from the group consisting of a toothpaste, dental cream, gel, tooth powder, odontic, mouthwash, pre-brushing rinse formulation, post brushing rinse formulation, chewing gum, lozenge, and candy. The oral care composition further comprises a fusion product between one or more SBDs and an enzyme selected from the group consisting of oxidases, peroxidases, proteases, lipases, glycosidases, lipases, esterases, deaminases, ureases and polysaccharide hydrolases. This oral care product can digest oral polysacchride and prevent formation of dental caries.

This invention further provides a method for sorting carbohydrate-containing molecules by using different $K_d$ values of carbohydrate binding domains. The carbohydrate-containing molecules may be a mixture of various glycoproteins, and the carbohydrates may be monosaccharide, disaccharide, or polysaccharide. For example, the users can sort glycoproteins by using starch-binding domains (SBDs) as a set of separator; maybe a column; with different $K_d$ values to generate a series of matrices with gradient ligand binding abilities. The SBDs may be obtainable from *Rhizopus* spp according to this invention, including wild type and mutants. The SBDs may be obtainable from the species which is known to have SBDs such as CBM family 21 and CBM family 20. These known species include *Arxula, Lipomyces, Aspergillus, Bacillus, Clostridium, Cryptococcus, Fusarium, Geobacillus, Neurospora, Pseudomonas, Streptomyces, Thielavia*, and *Thermoanaerobacter*.

Loading the sample into the set of separator, the SBD-bound molecules are kept in the column and the unbound molecules are excluded. Thus, the sample can be sorted into SBD-bound and unbound groups. Collecting unbound molecules in one container, and eluting SBD-bound molecules in another container, both can be further sorted. The further sorting methods may be based on chemical, physical or biological properties including liquid chromatography analysis, mass spectrometric analysis, lectin immunosensor techniques, two-dimensional gel electrophoresis, enzymatical techniques, and chemical derivatizations.

EXAMPLE

The following examples are offered by way of illustration and not by way of limitation.

Example 1

(A) Construction of SBD-6H

The gene encoding glucoamylase SBD from residues 26-131 was amplified by polymerase chain reaction (PCR) using the forward primer 5'-CATATGGCAAGTATTC-CTAGCAGT-3' and the reverse primer 5'-CTCGAGTGTA-GATACTTGGT-3' (restriction sites, shown in bold, were incorporated into the two primers). The PCR product was cloned into the pGEM-T Easy cloning vector (Promaga) and verified by DNA sequencing. The sbd gene fragment was subsequently ligated into pET23a(+) expression vector (Novagen) at NdeI and XhoI sites to generate pET-SBD. SBD-6H encoded by pET-SBD contains a C-terminal His$_6$ tag. The construct was transformed into competent *Escherichia coli* BL21-Gold (DE3) (Novagen) for protein expression.

(B) Expression and Purification of SBD-6H

BL21-Gold (DE3) cells transformed with pET-SBD were grown in LB medium containing 100 µg/ml ampicillin at 37° C. until the OD$_{600}$ reached 0.6. The temperature was then reduced to 20° C., and isopropyl β-D-thiogalactoside (IPTG) was added to a final concentration of 400 µM to induce recombinant protein expression. After further incubation for 16 h, cells were harvested by centrifugation at 3,700 g for 15 min at 4° C., the resultant pellet was resuspended in 20 ml of binding buffer (50 mM sodium acetate, pH 5.5) and then homogenized (EmulsiFlex-05 homogenizer). The cell debris was removed by centrifugation at 16,000 g for 15 min at 4° C. The supernatant was applied directly to the granular corn starch (pre-washed with binding buffer) and then incubated at 25° C. for 30 min with gentle shaking. The starch was washed with 10 column volumes of binding buffer twice and then eluted with 2 column volumes of elution buffer (50 mM glycine/NaOH, pH 10). The solution was dialyzed against binding buffer employing an Amicon stirred-cell concentrator (Millipore) equipped with a PM-10 membrane (10 kDa cut-off). Each fraction was analyzed by 15% SDS-PAGE gel and then stained with Coomassie brilliant blue. The protein concentrations were assayed by bicinchoninic acid (BCA) reagent kit (Pierce).

SBD-6H fused was expressed in *E. coli* BL21-Gold (DE3) at an optimized condition. After induction period, the soluble fraction was one-step purified by granular corn starch. Since low elution efficiency of SBD with maltose as elution agent employing previously reported methods was observed (Paldi et al. Biochem J (2003) 372: 905-910), here a substitute procedure for the elution of SBD with glycine/NaOH (pH 10) was adopted. Purified SBD-6H was analyzed by 15% SDS-PAGE and stained with Coomassie brilliant blue as shown in FIG. 1. SBD-6H derived from the signal step purification was homogeneous. This modified method enables fast and efficient purification of SBD from bacterial lysate with high purity (>98%) and yield (>90%).

Example 2

Effect of pH on Binding Ability and Stability

For the measurement of binding ability, SBD-6H and granular corn starch were incubated in buffers with varied pH values for 1 h as described in the starch binding assay. The stability was measured by keeping SBD-6H at 25° C. for 30 min in different buffers including glycine/HCl (pH 3), sodium acetate/acetic acid (pH4-5), $Na_2HPO_4/NaH_2PO_4$ (pH 6-7), Tris/HCl (pH 8) and glycine/NaOH (pH 9-10). The remaining binding ability was measured at 25° C. for 1 h in sodium acetate buffer (50 mM, pH 5.5). The relative binding ability of SBD-6H assayed at pH 5 was normalized as 100%.

Figure 2:
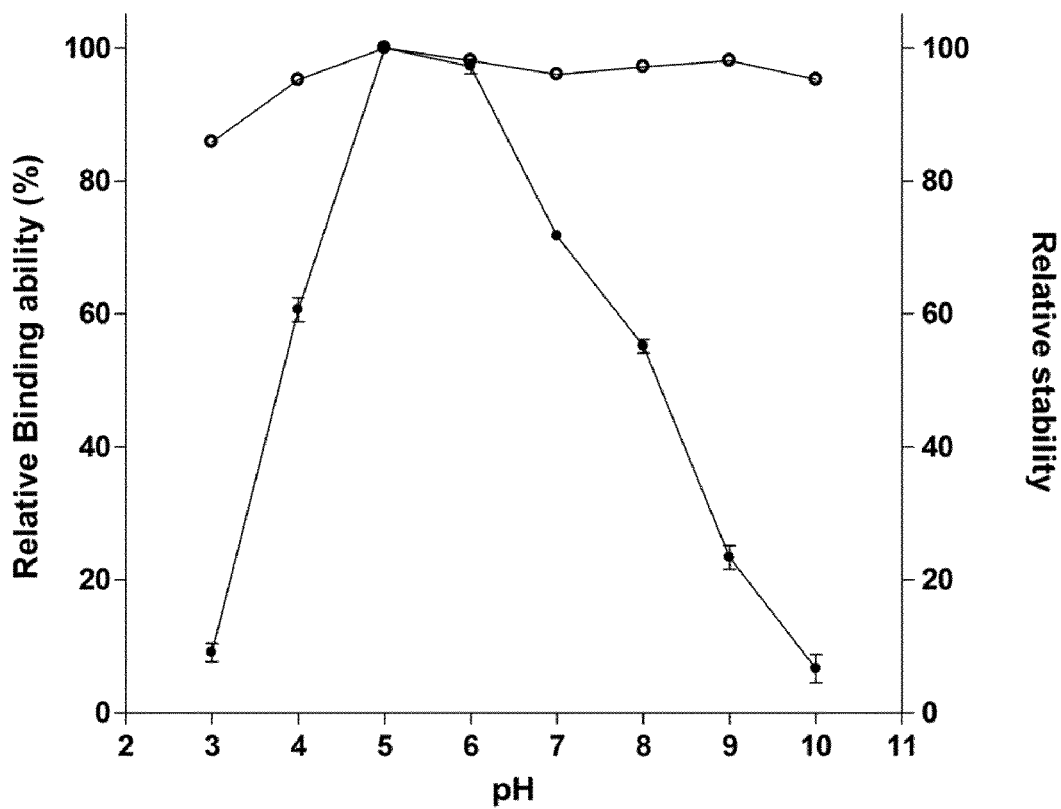
FIG. 2 illustrates effects of pH on binding ability and stability. The effects on binding ability (●) and stability (○) of the SBD-6H at varying pH are measured as described in the Experimental section. The relative binding ability of SBD-6H assayed in pH 5 is normalized as 100%.

The stability of SBD-6H was analyzed in the pH range from 3 to 10 and it indicated that the SBD-6H was stable in a wide pH range, even at the extreme acidic and alkaline conditions (FIG. 2). The binding assays were used to identify the optimal pH range of SBD-6H on adsorption of insoluble starch. As shown in FIG. 2, the pH range for maximal SBD-6H binding was 5 to 6, whereas relative binding ability at pH 4 and pH 8 was only 60.6% and 55.1%, respectively.

As shown in FIG. 2, SBD-6H was stable in a broad pH range, even at the extreme of the acidic and alkaline pH. It also indicated that the binding ability of SBD to starch was pH-dependence. The optimal pH for binding was around 5 to 6 similar to previous studies used maltose to release the SBD from starch even though maltose was not the optimal elution agent. Here, we had overcome this problem based on the properties of the pH-dependent binding ability. The elevated elution efficiency (>90%) was performed using an alkaline buffer as an elution agent.

Example 3

Association Rate of SBD-6H to Insoluble Starch

The purified SBD-6H in the concentration range from 15.6 to 27.2 µM was added to 1 mg/ml of pre-washed granular corn starch and incubated at 25° C. with gentle stir for 5 h. The binding was terminated at different time intervals by sedimentation of the starch. After centrifugation at 16,000 g for 10 min at 4° C., the protein concentration of the supernatant (unbound protein) was determined by the BCA assay, and the amount of bound protein was calculated from the difference between the initial and unbound protein concentrations. The bound protein at equilibrium expressed as micromole of protein per gram of starch was a linear function of the free (unbound) protein in the range of protein concentrations assayed.

Figure 3:
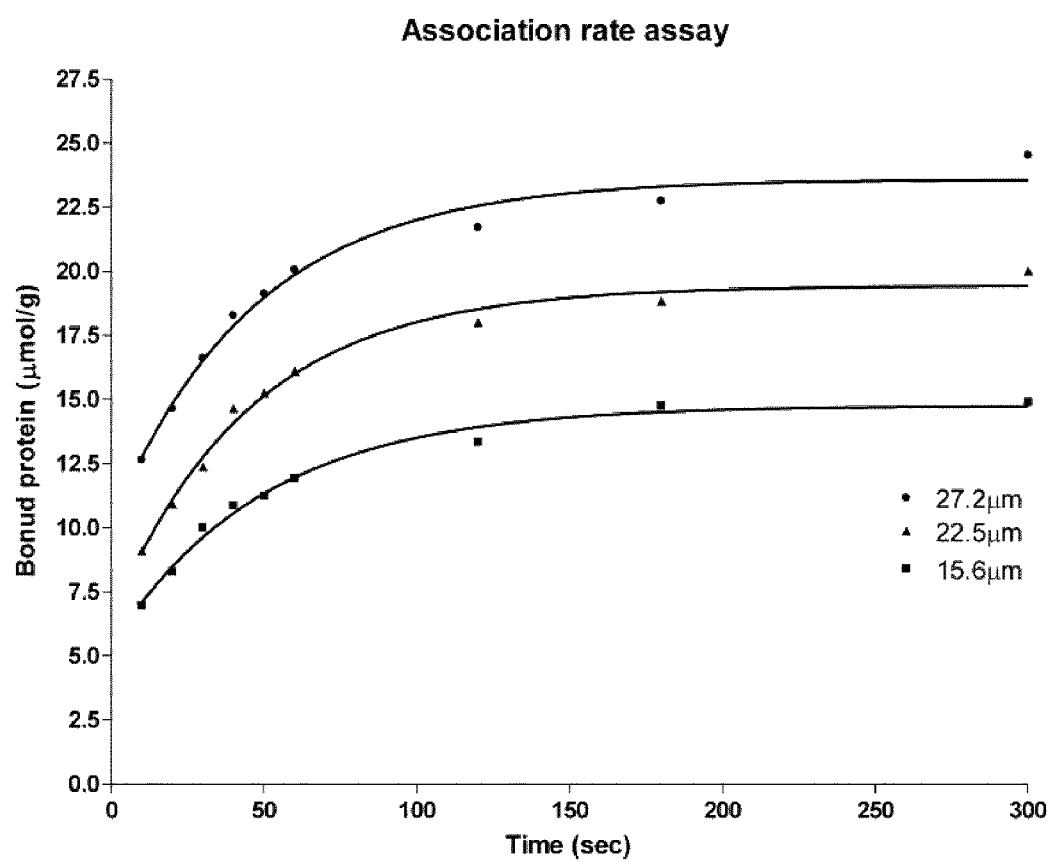
FIG. 3 illustrates adsorption rate of SBD-6H with insoluble starch. The association rate of SBD is analyzed by applying SBD-6H at different concentrations (■, 15.6 µM; ▲, 22.5 µM; ●, 27.2 µM) to corn starch for 5 h. Bound protein is calculated from the difference between the initial and unbound protein concentrations at different time points to determine the association rate.

The adsorption kinetics of SBD-6H to granular corn starch was performed at different protein concentrations as shown in FIG. 3. About 50% of the SBD-6H was bound to the insoluble starch during the first 10 min (relative to the amount of bound protein at equilibrium state). In the initial period (up to 40 min), the adsorption exhibited a linear phase. The amount of bound proteins was in proportion to the incubation time. Similar association rates (0.18±0.1 µmol/min·g), indicated by the initial slope of the binding curves at different SBD-6H concentrations were observed. After the linear phase (after 40 min), the bound protein increased slowly within prolonged incubation time. At the time of 120 min, more than 95% relative binding was reached. The time required for reaching the equilibrium was similar to *Aspergillus* SBDs (Paldi et al. Biochem J (2003) 372: 905-910).

Example 4

Starch Binding Assay

The starch-binding isotherm was analyzed as saturation binding assay: the SBD-6H was mixed with 1 mg/ml of pre-washed granular corn starch and incubated at 25° C. with gentle stir for 16 h. After centrifugation at 16,000 g for 10 min at 4° C., the amount of bound protein was calculated. Controls with protein but no starch were included to ensure that no precipitation occurred during the period of assay. The dissociation constant ($K_d$) and the maximal amount of bound protein ($B_{max}$) were determined by fitting to the non-linear regression of the binding isotherms, and equation (1) was used for one binding site saturation binding.

$$B=B_{max}F/(K_d+F) \quad (1)$$

where B (µmol) represents the bound protein; $B_{max}$ (µmol) was the maximal amount of bound protein; F (µmol) was the free protein in the system and $K_d$ (µmol) was the equilibrium dissociation constant. The units of the $B_{max}$ and $K_d$ values calculated were converted into µmol/g and µM, respectively.

SBD-Binding Affinity and Capacity

Figure 4:
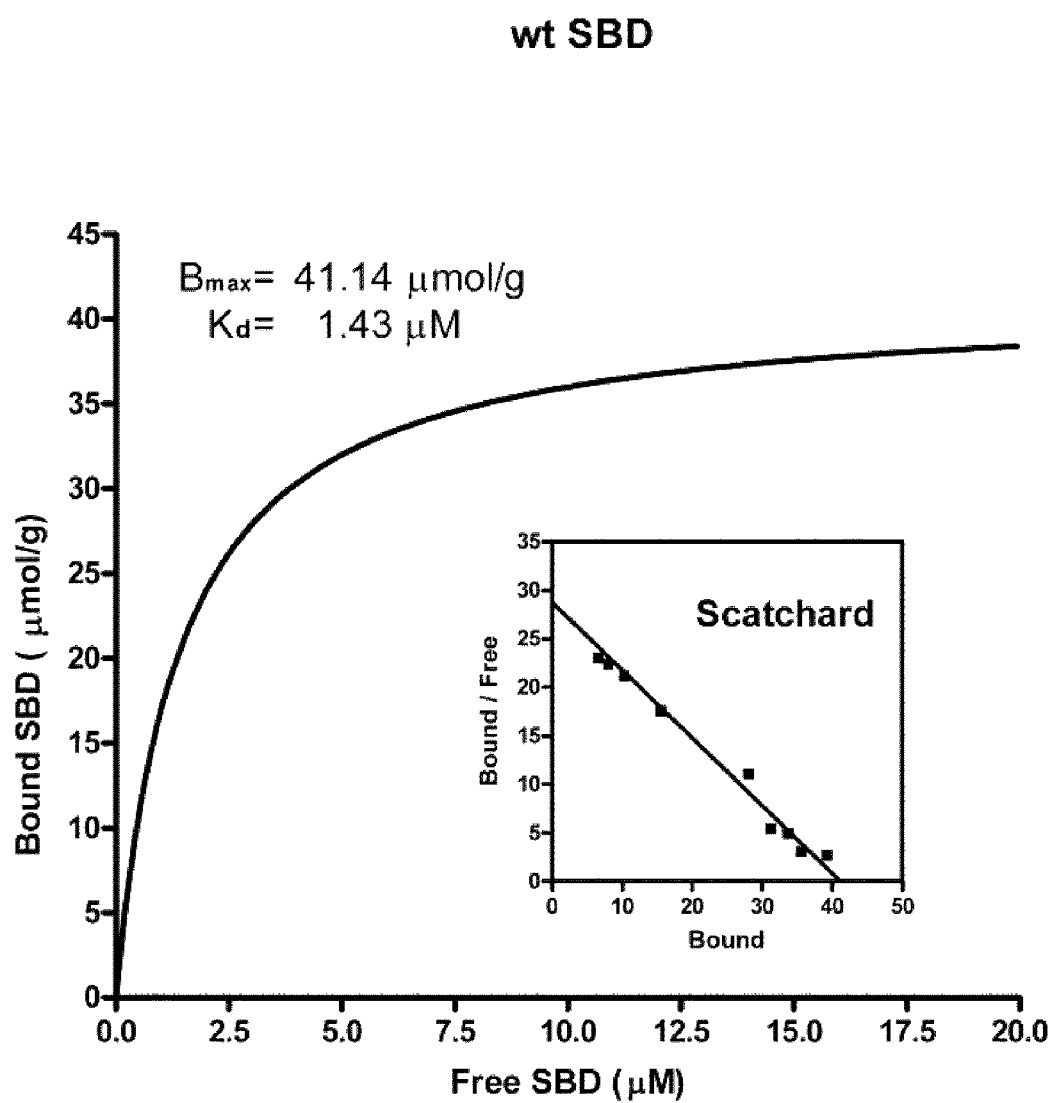
FIG. 4 illustrates $K_d$ and $B_{max}$ determination of the SBD-starch interaction. Starch binding assays are performed with granule corn starch at different protein concentrations. The $K_d$ and $B_{max}$ are determined by fitting to the non-linear regression of the binding isotherms for one binding site saturation binding.

Starch-binding isotherm as shown in FIG. 4 was used to study the affinity and capacity of purified SBD-6H. Equation (1) was used to calculate the non-linear regression curves of the equilibrium isotherm and determine the binding parameters ($B_{max}$ and $K_d$). The binding parameters, $K_d$ and $B_{max}$, determined by a two-parameter model for one binding site saturation binding, were 1.43±0.14 µM and 41.14±1.05 µmol/g, respectively. In addition, the dissociation constants from the engineered and proteolytically produced *Aspergillus* SBDs (3.2±0.9 µM and 12.7±0.5 µM respectively) were approximately 2-10 times higher than that of SBD-6H (Paldi et al. Biochem J (2003) 372: 905-910; Belshaw et al. FEBS Lett (1990) 269: 350-353). These observations indicate that SBD-6H has better binding affinity to insoluble starch than *Aspergillus* SBD. On the other hand, the $B_{max}$ values of the engineered and proteolytically produced *Aspergillus* SBDs (0.56 µmol/g and 1.08±0.02 µmol/g respectively) were markedly different from SBD-6H. The $K_d$ of SBD-6H is approximately 2-fold smaller than that of *Aspergillus* SBDs, whereas the $B_{max}$ of SBD-6H is markedly about 70-fold higher than that of *Aspergillus* SBDs These results indicated that both the starch-binding affinity and capacity of SBD-6H are grater than *Aspergillus* SBDs.

Example 5

(A) Construction of SBD-eGFP

Figure 5:
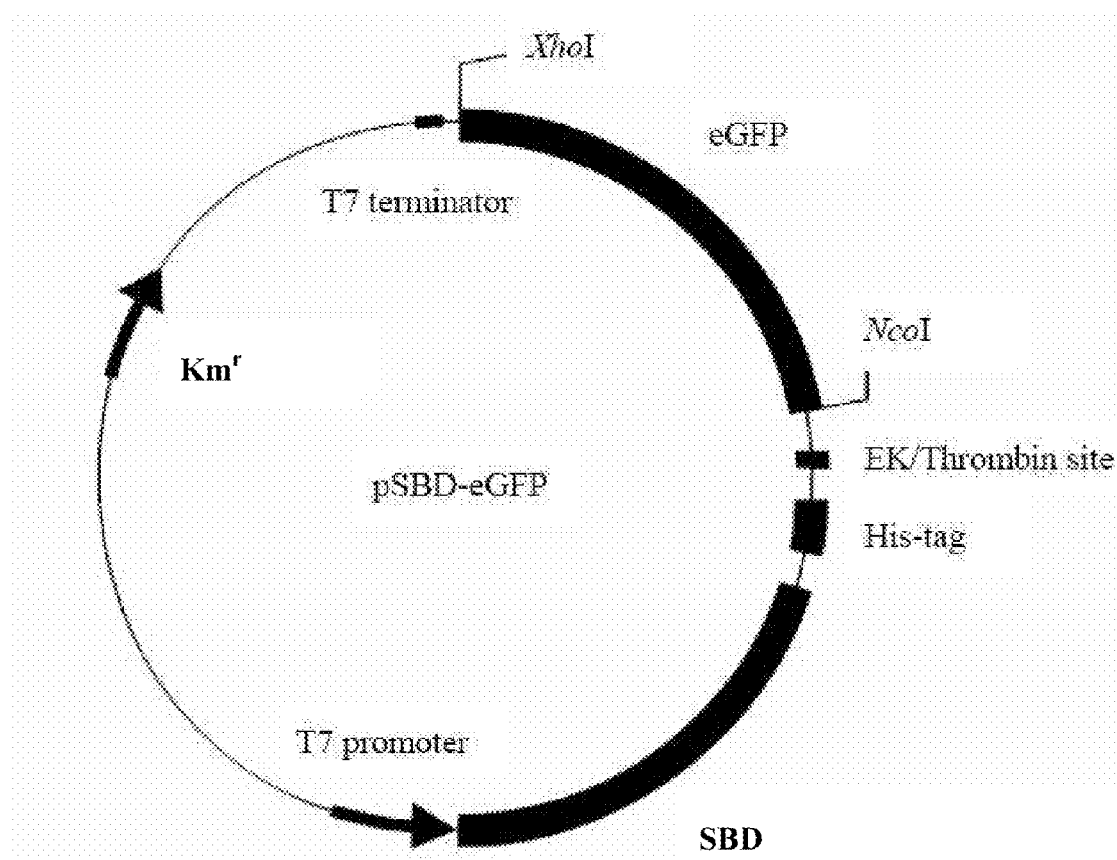
FIG. 5 shows construction of SBD-tagged fusion proteins. eGFP: gene encoding green fluorescent protein; SBD: starch binding domain; Km$^r$: kanamycin resistance gene.

The eGFP gene fragment was subsequently ligated into pET-SBD at NcoI and XhoI sites to generate pSBD-eGFP. The plasmid construct was as shown in FIG. 5. SBD-eGFP encoded by pSBD-eGFP contains a N-terminal SBD-6H and a C-terminal eGFP. The construct was transformed into competent *Escherichia coli* BL21-Gold (DE3) (Novagen) for protein expression.

(B) Expression and Purification of SBD-eGFP

BL21-Gold (DE3) cells transformed with pET-SBD were grown in LB medium containing 100 µg/ml ampicillin at 37° C. until the $OD_{600}$ reached 0.6. The temperature was then reduced to 20° C., and isopropyl β-D-thiogalactoside (IPTG) was added to a final concentration of 400 µM to induce recombinant protein expression. After further incubation for 16 h, cells were harvested by centrifugation at 3,700 g for 15 min at 4° C., the resultant pellet was resuspended in 20 ml of binding buffer (50 mM sodium acetate, pH 5.5) and then homogenized (EmulsiFlex-05 homogenizer). The cell debris was removed by centrifugation at 16,000 g for 15 min at 4° C. The supernatant was applied directly to the granular corn starch (pre-washed with binding buffer) and then incubated at 25° C. for 30 min with gentle shaking. The starch was washed with 10 column volumes of binding buffer twice and then eluted with 2 column volumes of elution buffer (50 mM glycine/NaOH, pH 10). The solution was dialyzed against binding buffer employing an Amicon stirred-cell concentrator (Millipore) equipped with a PM-10 membrane (10 kDa cut-off). Each fraction was analyzed by 15% SDS-PAGE gel and then stained with Coomassie brilliant blue. The protein concentrations were assayed by bicinchoninic acid (BCA) reagent kit (Pierce).

Figure 6:
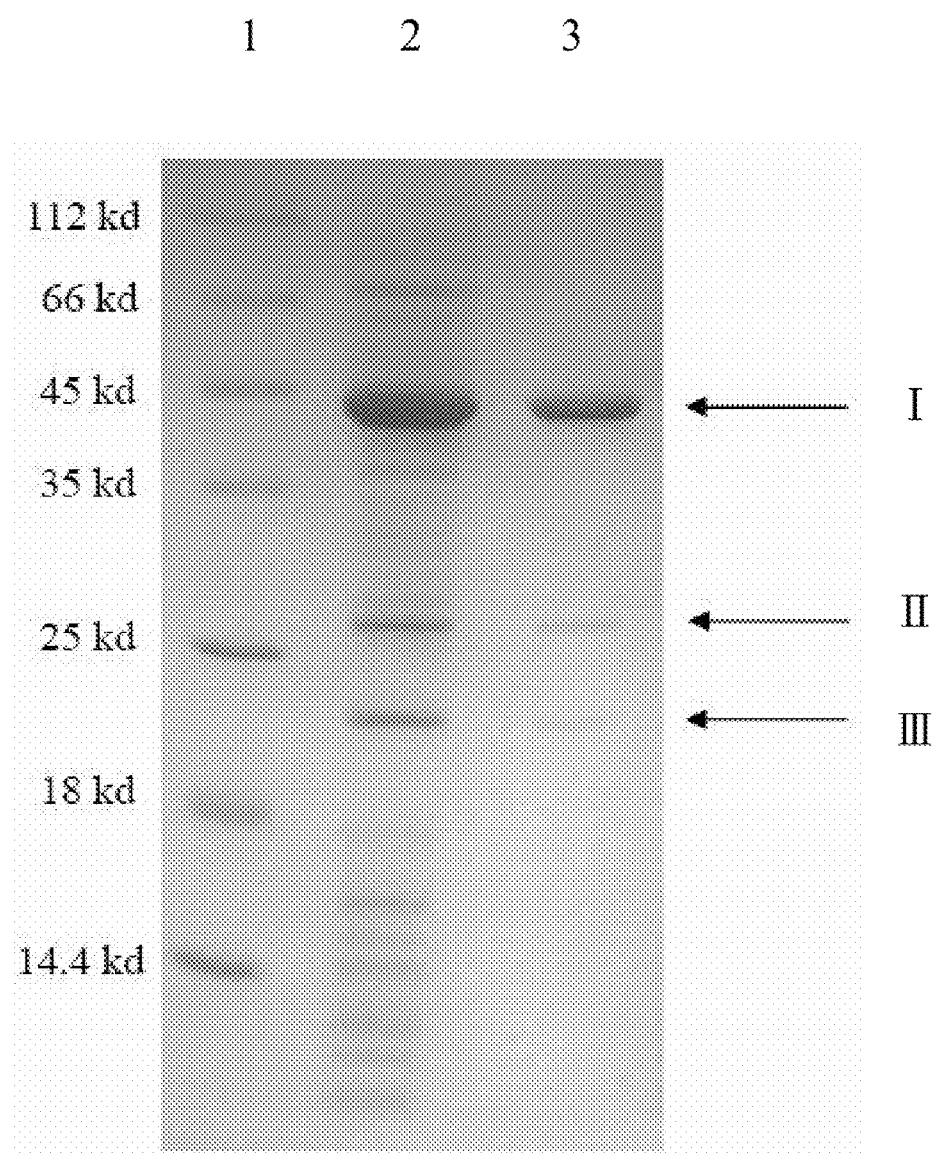
FIG. 6 illustrates purification of SBD-tagged fusion proteins using starch. The purified fusion protein is subjected to SDS/PAGE (15% gel) and the gel is stained with Coomassie Brilliant Blue R-250 for protein detection. Lane 1, molecular mass standards (molecular masses indicated at the left), lane 2, soluble fraction, and lane 3, elution. Arrowhead I: SBD-eGFP, arrowhead II: eGFP, and arrowhead III: SBD.

Purified SBD-eGFP was analyzed by 15% SDS-PAGE and stained with Coomassie brilliant blue as shown in FIG. 6.

What is claimed is:

1. A kit for purifying a recombinant protein comprises an expression vector, wherein the expression vector comprises a gene encoding starch binding domain selected from SEQ ID NO:1, SEQ ID NO:2 or SEQ ID NO:3.

2. The kit of claim 1, which further comprises an affinity matrix to bind the starch binging domain.

3. The kit of claim 1, which further comprises an elution buffer used to separate the recombinant protein and the affinity matrix.

4. The kit of claim 1, wherein the recombinant protein is an antibody, an antigen, a therapeutic protein, or an enzyme.

5. The kit of claim 2, wherein the affinity matrix is selected from the groups consisting of: mannose, starch, dextran, glucan, and a molecule containing glucose-glucose linkage structure.

6. The kit of claim 5, wherein the elution buffer is acidic or alkaline.

7. The kit of claim 1, wherein the recombinant protein is used for destruction or detection of a pathogen, or wherein the recombinant protein is used as a vaccine, or wherein the recombinant protein is used as an oral composition.

8. The kit of claim 7, wherein the oral care composition is selected from the group consisting of a toothpaste, dental cream, gel, tooth powder, odontic, mouthwash, pre-brushing rinse formulation, post brushing rinse formulation, chewing gum, lozenge, and candy.

9. The kit of claim 8, wherein the oral care composition further comprises a fusion product between one or more said starch binding domains and an enzyme selected from the group consisting of oxidases, peroxidases, proteases, lipases, glycosidases, lipases, esterases, deaminases, ureases and polysaccharide hydrolases.

10. The kit of claim 6, wherein the elution buffer further comprises a water-soluble sugar.

* * * * *

SEQUENCE LISTING

```
<160> NUMBER OF SEQ ID NOS: 3

<210> SEQ ID NO 1
<211> LENGTH: 107
<212> TYPE: PRT
<213> ORGANISM: Rhizopus oryzae
<220> FEATURE:
<221> NAME/KEY: DOMAIN
<222> LOCATION: (1)..(107)

<400> SEQUENCE: 1

Ala Ser Ile Pro Ser Ser Ala Ser Val Gln Leu Asp Ser Tyr Asn Tyr
 1               5                  10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser
            100                 105

<210> SEQ ID NO 2
<211> LENGTH: 107
<212> TYPE: PRT
<213> ORGANISM: Rhizopus oryzae
<220> FEATURE:
<221> NAME/KEY: DOMAIN
<222> LOCATION: (1)..(107)
<223> OTHER INFORMATION: Rhizopus oryzae wildtype_strain

<400> SEQUENCE: 2

Ala Ser Ile Pro Ser Ser Ala Ser Val Gln Leu Asp Ser Tyr Asn Tyr
 1               5                  10                  15

Asp Gly Ser Thr Phe Ser Gly Lys Ile Tyr Val Lys Asn Ile Ala Tyr
            20                  25                  30

Ser Lys Lys Val Thr Val Ile Tyr Ala Asp Gly Ser Asp Asn Trp Asn
        35                  40                  45

Asn Asn Gly Asn Thr Ile Ala Ala Ser Tyr Ser Ala Pro Ile Ser Gly
    50                  55                  60

Ser Asn Tyr Glu Tyr Trp Thr Phe Ser Ala Ser Ile Asn Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser
            100                 105
```

-continued

```
<210> SEQ ID NO 3
<211> LENGTH: 107
<212> TYPE: PRT
<213> ORGANISM: Rhizopus oryzae
<220> FEATURE:
<221> NAME/KEY: DOMAIN
<222> LOCATION: (1)..(107)
<223> OTHER INFORMATION: Rhizopus oryzae from U.S. Pat. No. 4863864

<400> SEQUENCE: 3

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Ile Tyr Ala Asn Gly Ser Asp Asn Trp Asn
        35                  40                  45

Asn Asn Gly Asn Thr Ile Ala Ala Ser Tyr Ser Ala Pro Ile Ser Gly
    50                  55                  60

Ser Asn Tyr Glu Tyr Trp Thr Phe Ser Ala Ser Ile Asn Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser
            100                 105
```